US007094776B2

(12) United States Patent
DeLuca et al.

(10) Patent No.: US 7,094,776 B2
(45) Date of Patent: *Aug. 22, 2006

(54) METHOD OF LOCKING 1α-OH OF VITAMIN D COMPOUNDS IN AXIAL ORIENTATION

(75) Inventors: Hector F. DeLuca, Deerfield, WI (US); Rafal R. Sicinski, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/083,628

(22) Filed: Mar. 18, 2005

(65) Prior Publication Data

US 2005/0182035 A1 Aug. 18, 2005

Related U.S. Application Data

(62) Division of application No. 10/241,555, filed on Sep. 11, 2002, now Pat. No. 6,890,914, which is a division of application No. 10/001,623, filed on Oct. 31, 2001, now Pat. No. 6,506,912, which is a division of application No. 09/553,206, filed on Apr. 20, 2000, now Pat. No. 6,369,099, which is a division of application No. 09/082,776, filed on May 21, 1998, now Pat. No. 6,114,317.

(51) Int. Cl.
*A01N 45/00* (2006.01)
*C07C 401/00* (2006.01)
(52) U.S. Cl. .................................... 514/167; 552/653
(58) Field of Classification Search ................ 514/167; 552/653
See application file for complete search history.

(56) References Cited

U.S. PATENT DOCUMENTS

| 4,666,634 | A | 5/1987 | Miyamoto et al. |
| 5,536,713 | A | 7/1996 | Deluca et al. |
| 5,877,168 | A | 3/1999 | Miyamoto et al. |
| 5,945,410 | A | 8/1999 | DeLuca et al. |
| 6,369,099 | B1 | 4/2002 | DeLuca et al. |

FOREIGN PATENT DOCUMENTS

| EP | 0184206 | 6/1986 |
| EP | 0516410 | 12/1992 |
| EP | 0387077 | 1/1994 |
| WO | WO 9601811 | 1/1996 |

OTHER PUBLICATIONS

Katsuhito et al, 6001 Chemical Abstracts, 2β-Substituted Vitamin D Derivatives, vol. 121, No. 21, 1994.

Fujishima et al, Synthesis and Biological Activity of 2-Methyl-20-EPI Analogues of 1α,25-Dihydroxyvitamin $D_3$, Bioorganic & Medicinal Chemistry Letters, vol. 8, No. 16, pp. 2145-2148, Aug. 18, 1998.

Konno et al, A Novel and Practical Route to A-Ring Enyne Synthon for 1α,25-Dihydroxyvitamin $D_3$ Analogs: Synthesis of A-Ring Diastereomers of 1α,25-Dihydroxyvitamin $D_3$ and 2-Methyl-1,25-Dihydroxyvitamin $D_3$, Bioorganic & Medicinal Chemistry Letters, vol. 8, No. 2, pp. 151-156, Jan. 20, 1998.

Okamura et al, Vitamin D: Concerning the Relationship Between Molecular Topology and Biological Function, Proc. Nat. Acada, Sci., U.S.A., Oct. 1974, vol. 71, No. 10, pp. 4194-4197.

Okano et al, Regulatory Activities of 2β-(3-Hydroxypropoxy)-1α,25-Dihydroxyvitamin $D_3$. A Novel Synthetic Vitamin $D_3$ Derivative on Calcium Metabolism, Biochemical and Biophysical Research Communications, vol. 163, No. 3, pp. 1444-1449, Sep. 29, 1989.

Posner et al, 2-Fluroalkyl A-Ring Analogs of 1,25-Dihydroxyvitamin $D_3$. Stereocontrolled Total Synthesis Via Intramolecular and Intermolecular Diels-Alder Cycloadditions. Preliminary Biological Testing, Journal of Organic Chemistry, vol. 60, No. 14, pp. 4617-4623, Jul. 14, 1995.

Posner et al, Stereocontrolled Synthesis of a Trihydroxylated A Ring as an Immediate Precursor to 1α,2α,25-Trihydroxyvitamin $D_3$, J. Org. Chem. 56, pp. 4339-4341, Apr. 15, 1991.

Sincinski et al, New 1α-25-Dihydroxy-19-Norvitamin $D_3$ Compounds of High Biological Activity: Synthesis and Biological Evaluation of 2-Hydroxymethyl, 2-Methyl, and 2-Methylene Analogues, Journal or Medicinal Chemistry, vol. 41, pp. 4662-4674, Oct. 22, 1998.

Sincinski et al, Synthesis, Conformational Analysis and Biological Activity of the 1α,25-Dihydroxy-10,19-Dihydrovitamin $D_3$ Isomers, Bioorganic Chemistry, vol. 22, pp. 150-171, 1994.

Trinh et al, Crystal Structure of 25-Hydroxy-Vitamin $D_3$ Monohydrate: A Stereo-chemical Analysis of Vitamin D Molecules, J. Org. Chem., 1977, pp. 393-401.

Trinh et al, Solid-State Conformations of Vitamin $D_3$, J. Org. Chem., vol. 41, No. 21, 1976, pp. 3476-3478.

*Primary Examiner*—Alton Pryor
(74) *Attorney, Agent, or Firm*—Andrus, Sceales, Starke & Sawall, LLP

(57) ABSTRACT

A method of modifying or altering the structure of a 1α-hydroxylated vitamin D compound to increase its biological activity by altering the conformational equilibrium of the A-ring to favor a chair conformation that presents the 1α-hydroxyl in the axial orientation. This is accomplished by either locking the A-ring chair conformation in a geometry having an axially orientated 1α-hydroxyl, or by the addition of one or more substituents to the A-ring which interact with other substituents in the molecule or on the A-ring to provide a driving force to the A-ring to adopt a chair conformation which presents the 1α-hydroxyl in the axial orientation.

19 Claims, No Drawings

METHOD OF LOCKING 1α-OH OF VITAMIN D COMPOUNDS IN AXIAL ORIENTATION

CROSS-REFERENCE TO RELATED APPLICATIONS

The present application is a divisional of U.S. patent application Ser. No. 10/241,555 filed Sep. 11, 2002 now U.S. Pat. No. 6,890,914 which in turn is a divisional of U.S. patent application Ser. No. 10/001,623 filed Oct. 31, 2001, now U.S. Pat. No. 6,506,912, which in turn is a divisional of U.S. patent application Ser. No. 09/553,206 filed Apr. 20, 2000, now U.S. Pat. No. 6,369,099, which in turn is a divisional of U.S. patent application Ser. No. 09/082,776 filed May 21, 1998, now U.S. Pat. No. 6,114,317.

STATEMENT REGARDING FEDERALLY SPONSERED RESEARCH OR DEVELOPMENT

This invention was made with United States government support awarded by the following agencies:
NIH Grant No. DK14881

The United States has certain rights in this invention.

BACKGROUND AND SUMMARY OF THE INVENTION

The present invention relates to vitamin D compounds, and more particularly, to a method of presenting the 1α-OH of vitamin D compounds in an axial orientation and the compounds made thereby.

The two diastereomeric forms of monosubstituted cyclohexanes (Scheme I) are differently populated, the equilibrium constant K being given by the equation $$\Delta G° = -RT \ln K$$

where K=[equatorial conformer]/[axial conformer]. $\Delta G°$ (usually negative) is the difference of free energy between the equatorial and axial conformers and $-\Delta G°$ is known as conformational free energy of the substituent R [defined as it's A value, Winstein et al., J. Am. Chem. Soc. 77, 5562 (1955)]. Thus, the greater the A value of the substituent R, the greater a driving force to adopt the R-equatorial form. A value can be, therefore, considered as

SCHEME I

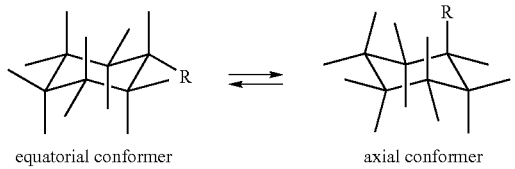

equatorial conformer      axial conformer destabilization energy imparted to a monosubstituted six-membered chair by an axial substituent. Thus, for example, the A value of methyl substituent equals ca. 1.7 kcal/mol [Hirsch, Top. Stereochem. 1, 199 (1967)] that corresponds to 95% of population of equatorial conformer of methylcyclohexane at room temperature. The conformational free energies of substituents in cyclohexanes under ideal conditions are expected to be additive. It is usually assumed that all conformational effects are additive, i.e. various destabilizing interactions identified within a six-membered ring system operate independently of each other. In di-, tri- and polysubstituted cyclohexanes mutual interactions among the substituents have to be considered. Such interactions can destabilize one chair conformation raising its energy to favor an alternate inverted chair form, or even favor some other, distorted (rigid or flexible) cyclohexane geometries. The most important interactions that influence the equilibrium between the respective chair conformations include interaction of a pair of substituents in 1,2-trans-diequatorial and 1,3-cis-diaxial relationship. Thus, total destabilization energy ($E_D$) can be described as a sum of the substituents' A values, representing monoaxial interactions, G values for 1,2-diequatorial interactions and U values for 1,3-diaxial interactions [Corey, et al., J. Org. Chem. 45, 765 (1980)].

$$E_D = \Sigma(A + G + U)$$

In the case of alkylidenecyclohexanes, additional interactions are involved, especially in 2-substituted derivatives. The most important interaction (designated $A^{1,3}$-strain, Johnson, Chem. Rev. 68, 375 (1968)] exists in the allylic segment between equatorial $R_1$ and substituent $R_2$ of the exomethylene unit (Scheme II). When both

SCHEME II

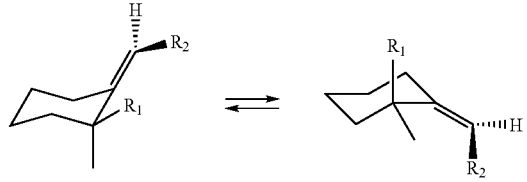

$R_1$ and $R_2$ are medium or large groups, the axial conformer is preferred over the equatorial (Malhotra et al., J. Am. Chem. Soc. 87, 5492 (1965)]. Thus, for example, when $R_1=R_2=Me$ the difference in energy between both forms is approximately 4.5 kcal/mol, in favor of the axial conformer. In the case when $R_1=Me$ and $R_2=H$, a 1:3 peri interaction exists which increases by ca. 1.25 kcal/mol the destabilization energy of the system (Duraisamy et al., J. Am. Chem. Soc. 105, 3264 (1983)].

Conformational behavior of vitamin D has attracted considerable attention over the past 25 years. It has been suggested long ago [Havinga, Experientia 29, 1181 (1973)] that vitamin D compounds can exist as a mixture of two rapidly equilibrating A-ring chair conformers. These two conformations were abbreviated as α- and β-forms (Scheme III). $^1$H NMR studies of vitamin $D_2$ and $D_3$ in chloroform solutions confirmed the existence of the dynamic equilibrium between the two chair forms [La Mar et al., J. Am. Chem. Soc. 96, 7317 (1974); Wing et al., J. Am. Chem. Soc. 97, 4980 (1975)] of these B-ring secosteroids. A similar conformational equilibrium has also been found for 25-hydroxyvitamin $D_3$ (25-OH-$D_3$), 1α-hydroxyvitamin $D_3$ (1α-OH-$D_3$) and the natural hormone 1α,25-dihydroxyvitamin $D_3$ (1α,25-(OH)$_2D_3$) as well as some other A-ring substituted vitamin D derivatives [see for example Helmer et al., Arch. Biochem. Biophys. 241, 608 (1985); Sheves et al., J. Org. Chem. 42, 3597 (1977); Berman et al., J. Org. Chem. 42, 3325 (1977); Sheves et al., J. Chem. Soc. Chem. Commun. 643 (1975); Okamura et al., J. Org. Chem. 43, 574 (1978)]. In the α-chair conformer of vitamin D molecule, the hydroxy group is equatorial whereas in the β-chair conformer the hydroxy group is axially oriented.

SCHEME III

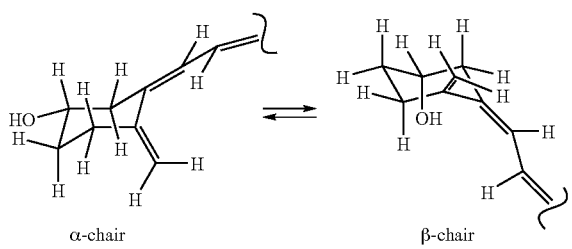

α-chair        β-chair

NMR studies of various vitamin D compounds in solutions have also shown that the ratio of the respective A-ring conformers depends significantly on the solvent used [Helmer et al., Arch. Biochem. Biophys. 241, 608 (1985)]. Unfortunately, due to solubility problems, it is impossible to study these conformer populations in an aqueous medium. X-Ray diffraction studies of vitamin $D_2$ and $D_3$ confirmed that their A-rings also occur in the solid phase as an equimolar mixture of such extreme α- and β-chair conformations [Hull et al., Acta Cryst., Sect. B, 32, 2374 (1976); Trinh et al., J. Org. Chem. 41, 3476 (1976)]. Interestingly, 25-OH-$D_3$ exists in the solid state exclusively in the α-form whereas the natural hormone 1α,25-$(OH)_2D_3$ in the A-ring β-form [Trinh et al., J. Chem. Soc., Perkin Trans. II, 393 (1977); Suwinska et al., Acta Cryst., Sect. B, 52, 550 (1996)]. X-Ray studies have also shown that the C(5)=C(6)-C(7)=C(8) diene part of the molecule is nearly planar, whereas the exocyclic C(10)=C(19) bond, because of steric strain, is twisted out of plane by about 55°. This exomethylene group is situated below the mean A-ring plane in the α-chair form and above it in the alternate β-chair form. In the case of vitamin D analogs substituted in the ring A with a 1α-hydroxy group, crucial for biological activity, the orientation of 1α-OH is axial in the a chair form and equatorial in the β-form (Scheme IV).

SCHEME IV

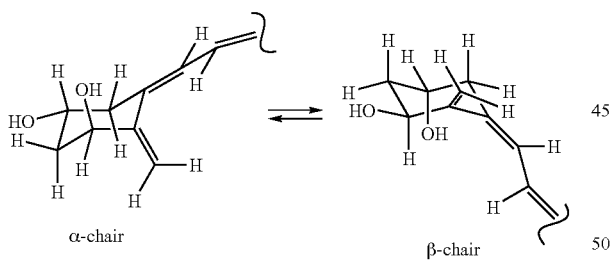

α-chair        β-chair

It has to be added that molecular mechanics calculations revealed that, similarly as in the case of the model 1,2-dimethylenecyclohexane ([Hofmann et al., J. Org. Chem. 55, 2151 (1990)], an existence of other than low-energy chair conformations of the ring A can be expected for D vitamins, namely, half-chair or twist forms [Mosquera et al., J. Mol. Struct. 168, 125, (1988); Hofer et al., Monatsh. fur Chemie, 124, 185 (1993)].

In 1974, it was proposed [Okamura et al., Proc. Natl. Acad. Sci. USA 71, 4194 (1974); Wing et al., Science 186, 939 (1974)] that calcium regulation ability of vitamin D is limited to the compounds that can assume a ring-A chair conformation in which the 1α-hydroxy group (or pseudo-1α-OH) occupies an equatorial orientation. Such conformation, according to this hypothesis, has the proper geometry for binding to the protein receptor, a step which is necessary to induce the biological response leading to the calcium transport and calcium mobilization in the body. However, recent results of biological testing of 1α,25-dihydroxy-10,19-dihydroxyvitamin $D_3$ compounds do not support the idea that the equatorially favored 1-hydroxyl would be the most biologically active. On the contrary, 1α,25-dihydroxy-10(S),19-dihydrovitamin $D_3$, the analog strongly biased toward the A-ring chair conformer possessing 1α-axial orientation, provided the greatest in vivo biological response and showed very significant activity on intestinal calcium transport. Moreover, more recent studies on 19-norvitamins, especially those substituted at C-2, demonstrate that pronounced biological activity is provided by compounds having an axial 1α-hydroxyl. Thus, it is believed that axial orientation of the 1α-hydroxyl group in the vitamin D molecule is of crucial importance for its biological activity and, the prediction of its biological response can be made by evaluation of the conformational equilibrium of the A-ring of the vitamin. It is believed that the more favored the axial position of 1α-hydroxyl is the greater biological response can be expected. A logical extension of this prediction is that the greatest activity can be predicted for such A-ring substitution of vitamin D molecules which:

1) constitute anancomeric system or other corresponding to at least 90% preponderating conformer possessing 1α-OH in axial position, even though the rate of A-ring inversion can remain facile—these analogs are characterized by conformationally free well-defined geometries of A rings and a significant energy advantage (at least 1.2 kcal/mole) for an axial 1α-OH conformer; or 2) constitute conformationally locked, rigid or distorted geometries in which the A ring is held in only one chair conformation, i.e. the one having an axial 1α-OH or, although it may deform considerably, it may not flip over to its conformationally inverted opposite form with equatorial orientation of 1α-OH.

Such structural constrains which prevent the cyclohexane ring from flipping but which can be accommodated by its chair geometry (Scheme V) include:

1) anchoring bonds (trans-fusion bonds to a ring of size seven or smaller),
2) flattening bonds (fusion bonds to a ring of size seven or smaller which contains a double bond exocyclic to the six-membered ring), and
3) bridged bonds (two contiguous ring bonds whose termini are joined by a bridge of five atoms or fewer).

SCHEME V anchoring bonds        flattening bonds

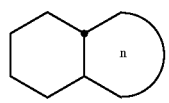        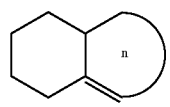

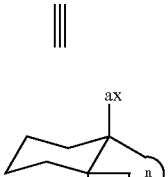

$n \leq 7$        $n \leq 7$

-continued bridged bonds

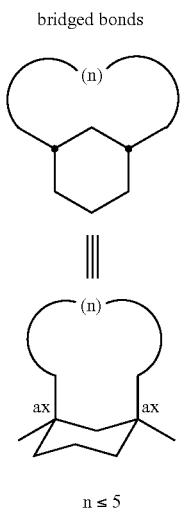

n ≤ 5

It should be noted that the remaining substituents (or hydrogens) of flattening or anchoring bonds must assume an axial orientation with respect to the six-membered ring. In the case of (1,3)-bridging, the bridged bonds have to be axially disposed with respect to the six-membered ring.

Accordingly, the present invention provides a novel class of 1α-hydroxylated vitamin D compounds wherein the conformational equilibrium of the A-ring has, or has been altered or modified to favor a chair conformation that presents the 1α-hydroxyl in the axial orientation, and the A-ring is attached to the conventional 5,7-diene and C-D ring system having any known side chain attached at carbon 17 of the D-ring.

Structurally these novel analogs are characterized by the general formula I shown below:

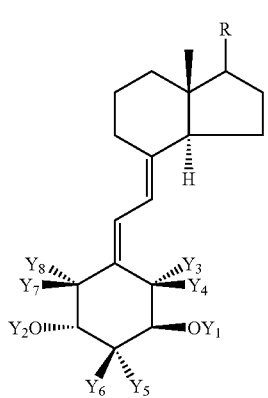

I where $Y_1$ and $Y_2$, which may be the same or different, are each selected from the group consisting of hydrogen and a hydroxy-protecting group; where $Y_3$, $Y_4$, $Y_5$, $Y_6$, $Y_7$ and $Y_8$, which may be the same or different, are each selected from the group consisting of hydrogen, a methyl group or substituted methyl group of the formula —$CR_1R_2R_3$, an amino group or substituted amino group of the formula —$NR_1R_2$, a phosphino group or substituted phosphino group of the formula —$PR_1R_2$, an alkylsulfinyl group, an arylsulfinyl group, an alkylsulfonyl group, an arylsulfonyl group, and aryl, where $R_1$, $R_2$ and $R_3$ are each independently selected from the group consisting of hydrogen, $C_{1-5}$ alkyl, hydroxyalkyl, aminoalkyl, halogenalkyl, alkoxyalkyl, aryloxyalkyl, aryl, halogen, hydroxyl, protected hydroxy, alkoxyl, aryloxyl, acyl, an amino group, an alkyl substituted amino group, and an aryl substituted amino group, and where $R_1$ and $R_2$ taken together represent an oxo group or a group —$(CH_2)_m$— where m is an integer having a value of from 2 to 5; or $Y_3$ and $Y_4$ when taken together represent a methylene group; or $Y_7$ and $Y_8$ when taken together represent a methylene group; where $Y_2$ and $Y_6$, or $Y_2$ and $Y_7$, when taken together may represent the group —$(CR_1R_2)_n$— where n is an integer having a value of from 1 to 4 and wherein any of the groups —$CR_1R_2$— may be replaced by an oxygen, sulfur or nitrogen atom; where $Y_5$ and $Y_8$, or $Y_5$ and $Y_3$, or $Y_3$ and $Y_8$, when taken together may represent the group —$(CR_1R_2)_r$— where r is an integer having a value of from 1 to 5 and wherein any of the groups —$CR_1R_2$— may be replaced by an oxygen, sulfur or nitrogen atom; and where $Y_5$ and $Y_6$ when taken together represent the group =$CR_4R_5$ where $R_4$ and $R_5$, which may be the same or different, are each selected from the group consisting of hydrogen and $Y_3$, with the proviso that $R_4$ and $R_5$ cannot be a hydroxyl; and where $R_4$ and $Y_2$ when taken together may represent the group —$(CR_1R_2)_s$— where s is an integer having a value of from 1 to 3; and where the group R represents any of the typical side chains known for vitamin D type compounds.

More specifically R can represent a saturated or unsaturated hydrocarbon radical of 1–35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below

where the stereochemical center (corresponding to C-20 in steroid numbering) may have the R or S configuration, (i.e. either the natural configuration about carbon 20 or the 20-epi configuration), and where Z is selected from Y, —OY, —$CH_2OY$, —C≡CY and —CH=CHY, where the double bond may have the cis or trans geometry, and where Y is selected from hydrogen, methyl, —$COR_{10}$ and a radical of the structure:

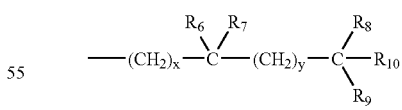

where x and y, independently, represent the integers from 0 to 5, where $R_6$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R_7$, $R_8$, and $R_9$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R_6$ and $R_7$, taken together, represent an oxo group, or an alkylidene group, $=CR_7R_8$, or the group —$(CH_2)_p$—, where p is an integer from 2 to 5, and where $R_8$ and $R_9$, taken together, represent an oxo group, or the group —$(CH_2)_q$—, where q is an integer from 2 to 5, and where $R_{10}$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH($CH_3$)—, —CH($R^3$)—, or —CH($R^2$)— at positions 20, 22, and 23, respectively, may be replaced by an oxygen or sulfur atom.

The wavy line to the substituent at C-20 indicates that the carbon 20 may have either the R or S configuration.

Specific important examples of side chains with natural 20R-configuration are the structures represented by formulas (a), (b), (c), (d) and (e) below, i.e. the side chain as is occurs in 25-hydroxyvitamin $D_3$ (a); vitamin $D_3$ (b); 25-hydroxyvitamin $D_2$ (c); vitamin $D_2$ (d); and the C-24 epimer of 25-hydroxyvitamin $D_2$ (e):

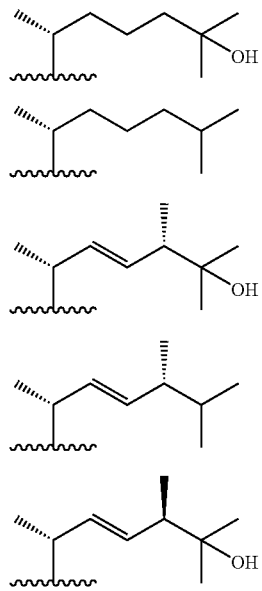

The above novel compounds wherein the 1α-OH group is presented in the axial orientation exhibit a desired, and highly advantageous, pattern of biological activity. These compounds are characterized by having greater biological activity, as compared to 1α,25(OH)$_2$D$_3$, in one or more of the three activities typically referred to as "calcemic" activities, i.e. intestinal calcium transport activity, bone mineralization activity and bone calcium mobilization activity, or in cell differentiation activity. Hence, these compounds may be highly specific in their calcemic activity. Their preferential calcemic activity suggests the in vivo administration of these compounds for the treatment of metabolic bone diseases where bone loss is a major concern. Because of their preferential calcemic activity on bone, one or more of these compounds may be preferred therapeutic agents for the treatment of diseases where bone formation is desired, such as osteoporosis, especially low bone turnover osteoporosis, steroid induced osteoporosis, senile osteoporosis or post-menopausal osteoporosis, as well as hypoparathroidism, osteomalacia and renal osteodystrophy. In addition, hypocalcemia as well as rickets, and vitamin D resistant rickets may be treated with one or more of the disclosed compounds. These compounds may also provide a method of treating female infertility in female mammals. The treatment may be transdermal, oral (in solid or liquid form) or parenteral. The compounds may be present in a composition in an amount from about 0.01 µg/day to about 100 µg/day, preferably about 0.1 µg/gm to about 50 µg/gm of the composition, and may be administered in dosages of from about 0.1 µg/day to about 50 µg/day.

The compounds of the invention are also especially suited for treatment and prophylaxis of human disorders which are characterized by an imbalance in the immune system, e.g. in autoimmune diseases, including multiple sclerosis, diabetes mellitus, host versus graft reaction, and rejection of transplants; and additionally for the treatment of inflammatory diseases, such as rheumatoid arthritis and asthma, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with one or more of the compounds of the invention.

The above compounds may also be characterized by high cell differentiation activity. Thus, these compounds may also provide therapeutic agents for the treatment of psoriasis and other skin disorders characterized by proliferation of undifferentiated skin cells, e.g. dermatitis, eczema, solar keratosis and the like, or as an anti-cancer agent, especially against leukemia, colon cancer, breast cancer and prostate cancer. The compounds may be present in a composition to treat disorders such as psoriasis in an amount from about 0.01 µg/gm to about 100 µg/gm of the composition, and may be administered topically, transdermally, orally (in solid or liquid form) or parenterally in dosages of from about 0.01 µg/day to about 100 µg/day.

This invention also provides a novel method of modifying or altering the structure of a 1α-hydroxylated vitamin D compound to increase its biological activity by altering the conformational equilibrium of the A-ring of the 1α-hydroxylated vitamin D compound to favor a chair conformation that presents the 1α-hydroxyl in the axial orientation. This is accomplished by either locking the chair conformation of the A-ring in a geometry having an axially orientated 1α-hydroxyl, or by the addition of one or more substituents to the A-ring which interact with other substituents in the molecule or on the A-ring to provide a driving force to the A-ring to adopt a chair conformation which presents the 1α-hydroxyl in the axial orientation.

DETAILED DESCRIPTION OF THE INVENTION

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description of the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl", "aminoalkyl", "halogenalkyl", "alkoxyalkyl", "aryloxyalkyl", and "fluoroalkyl" refer to an alkyl radical substituted by one or more hydroxy, deuterium, amino, halogen, alkoxy, aryloxy, or fluoro group respectively. A "halogen" group includes any of the five elements fluorine, chlorine, bromine, iodine and astatine that form a part of group VIIA of the periodic table.

As previously discussed, the novel analogs of the present invention are characterized by the general formula I shown below:

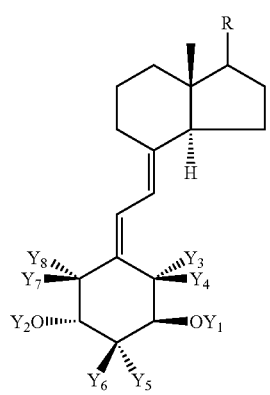

I where the definitions of $Y_1$, $Y_2$, $Y_3$, $Y_4$, $Y_5$, $Y_6$, $Y_7$, $Y_8$ and R are as previously set forth herein. The preferred analogs are the following:

1. 2-Substituted 1α-hydroxy Vitamin D Compounds 1.1. 2α-Substitution

Vitamins possessing 2α-substituent U that is characterized by large conformational free energy (A value) and, therefore having this C(2) substituent in equatorial disposition and, therefore, having 1α-hydroxyl in an axial orientation:

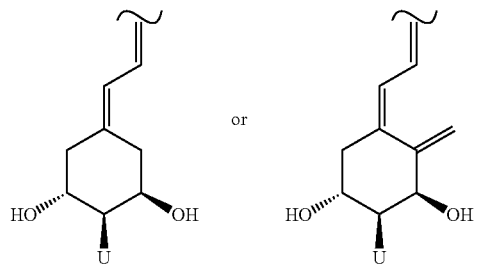

-continued

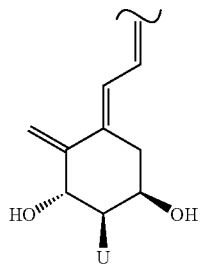

where U is selected from the group consisting of a methyl, a substituted methyl group described by general formula $CR_1R_2R_3$, an amino group or substituted amino group described by general formula $NR_1R_2$, a phosphino group or substituted phosphino group described by general formula $PR_1R_2$, an alkyl- or arylsulfinyl group, an alkyl- or arylsulfonyl group, and aryl, and where $R_1$, $R_2$ and $R_3$ are each independently selected from the group consisting of hydrogen, alkyl, hydroxyalkyl, aminoalkyl, halogenalkyl, alkoxyalkyl, aryloxyalkyl, aryl, halogen, hydroxyl, protected hydroxy, alkoxyl, aryloxyl, acyl, an amino group, an amino group substituted with alkyl or aryl substitutents and where $R_1$ and $R_2$, taken together, represent an oxo group, or a group $-(CH_2)_m-$ where m is an integer having a value of from 2 to 5.

1.2. 2α-Substitution and Formation of a Ring with 3β-O

Vitamins that contain an anchoring bond system, i.e., possessing an additional ring connecting C(2) with C(3)-O. The vitamins are characterized by trans-diequatorial orientation of substituents at C(2) and C(3) and, therefore, they have 1α-hydroxyl in an axial orientation.

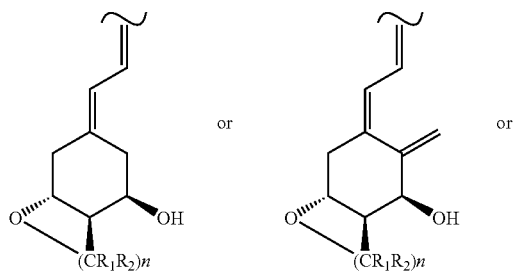

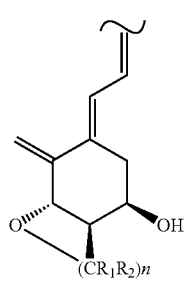

where $R_1$ and $R_2$ are as described above, and wherein n is an integer having a value of from 1 to 4, and wherein any of the groups $CR_1R_2-$ may be replaced by an oxygen, sulfur or nitrogen atom.

1.3. 2-alkylidene Compounds

Vitamins in which 2-methylene group is further substituted by U. The vitamins are characterized by cis-orientation of substituents of the terminal olefinic atoms of the 1,4-dimethylenecyclohexane system of the ring A, i.e. trans-orientation between C(6)-C(7) bond and C(1')-U bond. Substituent U due to its size strongly interacts with equatorial 1α-OH and, therefore, the inverted A-ring chair conformer is favored, having 1α-hydroxyl in an axial orientation:

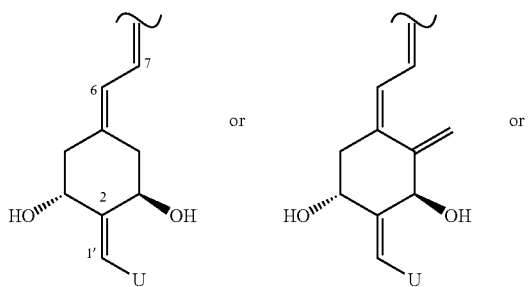

or

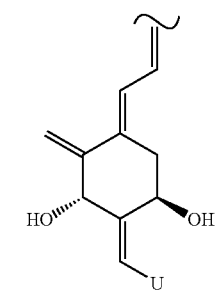

where U is as described above with the proviso that U cannot be an —OH group.

1.4. 2-alkylidene Compounds with an Additional Connection with 3β-O.

Vitamins that contain a flattening bond system, i.e., an exocyclic 2-methylene group that is further substituted and forms a ring with C(3)-O. The vitamins are characterized by trans-orientation of substituents of the terminal olefinic atoms of the 1,4-dimethylenecyclohexane system of the ring A, i.e., trans-orientation between C(6)-C(7) bond and C(1')-C(2')$R_1R_2$ bond. Therefore, these vitamins have C(3)-O substituent in equatorial disposition and 1α-hydroxyl in an axial orientation:

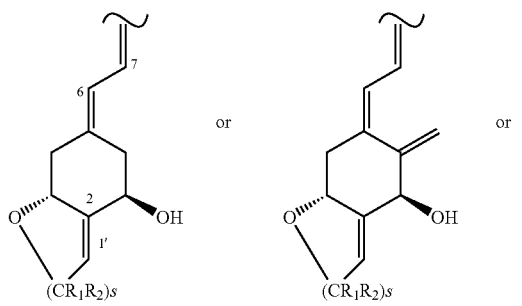

or

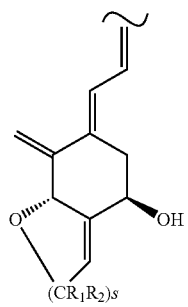

where $R_1$ and $R_2$ are as described above, and wherein s is an integer having a value of from 1 to 3, and wherein any of the groups —$CR_1R_2$— may be replaced by an oxygen, sulfur or nitrogen atom.

2. 4α-Substitution and Formation of a Ring with 3β-O

Vitamins that contain an anchoring bond system, i.e., possessing an additional ring connecting C(4) with C(3)-O. The vitamins are characterized by trans-diequatorial orientation of substituents at C(3) and C(4) and, therefore, they have 1α-hydroxyl in an axial orientation:

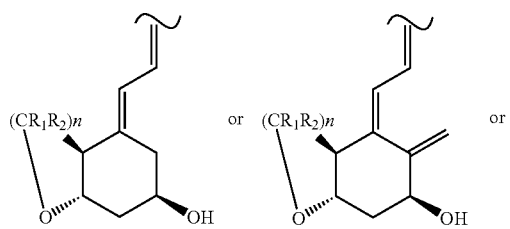

or

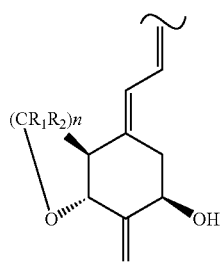

where $R_1$ and $R_2$ are as described above, and wherein n is an integer having a value of from 1 to 4, and wherein any of the groups —$CR_1R_2$— may be replaced by an oxygen, sulfur or nitrogen atom.

3. 10β-Substitution

Vitamins possessing 10β-substituent U, which due to its size strongly interacts with C(7)-H and, therefore, the inverted A-ring chair conformer is favored, having 1α-hydroxyl in an axial orientation:

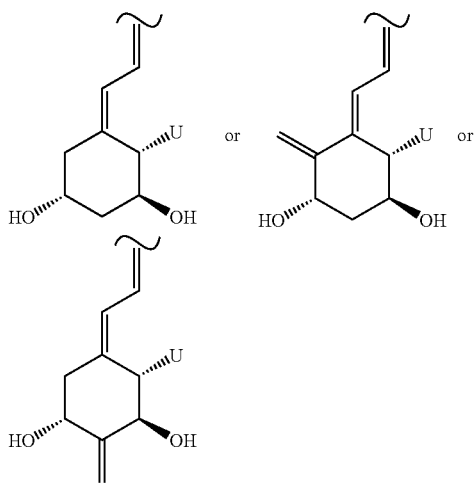

where U is as described previously.

4. 1,3-diaxially Bridged Compounds

4.1. 2β,4β-Bridged

Vitamins that contain a bridged bond system, i.e., possessing an additional ring connecting C(2) with C(4). The vitamins are characterized by cis-1,3-diaxial orientation of additional substituents at C(2) and C(4) and, therefore, they have 1α-hydroxyl in an axial orientation:

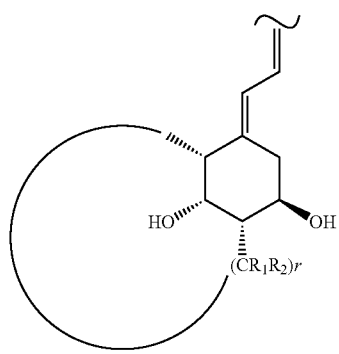

or

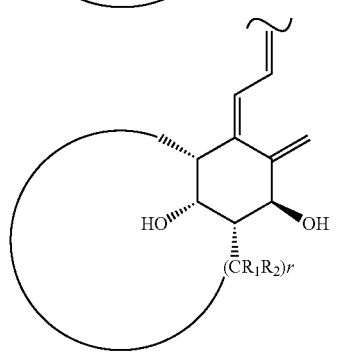

where $R_1$ and $R_2$ are as described above, and wherein r is an integer having a value of from 1 to 5, and wherein any of the groups —$CR_1R_2$— may be replaced by an oxygen, sulfur or nitrogen atom.

4.2. 2β,10β-Bridged

Vitamins that contain a bridged bond system, i.e., possessing an additional ring connecting C(2) with C(10). The vitamins are characterized by cis-1,3-diaxial orientation of substituents at C(2) and C(10) and, therefore, they have 1α-hydroxyl in an axial orientation:

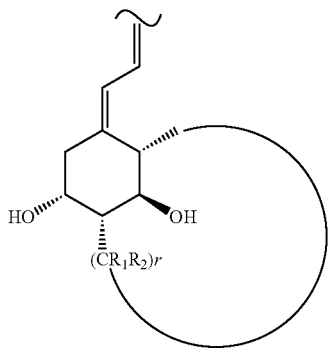

or

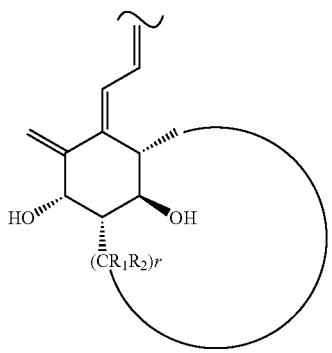

where $R_1$ and $R_2$ are as described above, and wherein r is an integer having a value of from 1 to 5, and wherein any of the groups —$CR_1R_2$— may be replaced by an oxygen, sulfur or nitrogen atom.

4.3 4β,10β-Bridged

Vitamins that contain a bridged bond system, i.e., possessing an additional ring connecting C(4) with C(10). The vitamins are characterized by cis-1,3-diaxial orientation of additional substituents at C(4) and C(10) and, therefore, they have 1α-hydroxyl in an axial orientation:

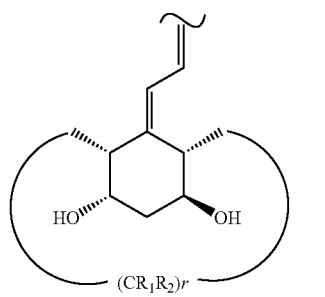

or

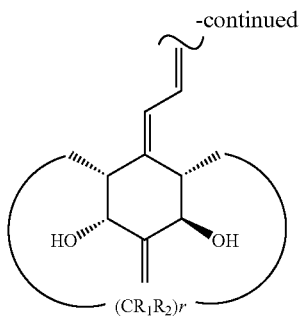

where $R_1$ and $R_2$ are as described above, and wherein r is an integer having a value of from 1 to 5, and wherein any of the groups —$CR_1R_2$— may be replaced by an oxygen, sulfur or nitrogen atom.

Methods of making compounds of formulae I and 1.1–4.3 are known. Specifically, reference is made to Zhu et al, Chem. Rev. 95, 1877 (1995) and Dai et al, Synthesis 1383 (1994) which describe a method of synthesizing such compounds.

It should be noted in this description that the term "24-homo" refers to the addition of one methylene group and the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at carbon 26 and 27 positions so that for example $R^3$ and $R^4$ are ethyl groups. Likewise, the term "26,27-diethyl" refers to the addition of an ethyl group at the 26 and 27 positions so that $R^3$ and $R^4$ are propyl groups.

In the following lists of compounds, the particular substituents attached on the A-ring should be added to the nomenclature. For example, if a methyl group is the alkyl substituent attached at the carbon 2 position on the A-ring, the term "2-methyl" should precede each of the named compounds. If an ethyl group is the alkyl substituent attached at the carbon 2 position on the A-ring, the term "2-ethyl" should precede each of the named compounds, 1 and so on. In addition, if the methyl group attached at the carbon 20 position is in its epi or unnatural configuration, the term "20(S)" or "20-epi" should be included in each of the following named compounds. The named compounds could also be of the vitamin $D_2$ type if desired.

Specific and preferred examples of the compounds of structure I when the side chain is unsaturated are:
19-nor-24-homo-1,25-dihydroxy-22-dehydrovitamin $D_3$;
19-nor-24-dihomo-1,25-dihydroxy-22-dehydrovitamin $D_3$;
19-nor-24-trihomo-1,25-dihydroxy-22-dehydrovitamin $D_3$;
19-nor-26,27-dimethyl-24-homo-1,25-dihydroxy-22-dehydrovitamin $D_3$;
19-nor-26,27-dimethyl-24-dihomo-1,25-dihydroxy-22-dehydrovitamin $D_3$;
19-nor-26,27-dimethyl-24-trihomo-1,25-dihydroxy-22-dehydrovitamin $D_3$;
19-nor-26,27-diethyl-24-homo-1,25-dihydroxy-22-dehydrovitamin $D_3$;
19-nor-26,27-diethyl-24-dihomo-1,25-dihydroxy-22-dehydrovitamin $D_3$;
19-nor-26,27-diethyl-24-trihomo-1,25-dihydroxy-22-dehydrovitamin $D_3$;
19-nor-26,27-dipropyl-24-homo-1,25-dihydroxy-22-dehydrovitamin $D_3$;
19-nor-26,27-dipropyl-24-dihomo-1,25-dihydroxy-22-dehydrovitamin $D_3$; and
19-nor-26,27-dipropyl-24-trihomo-1,25-dihydroxy-22-dehydrovitamin $D_3$.

Specific and preferred examples of the compounds of structure I when the side chain is saturated are:
19-nor-24-homo-1,25-dihydroxyvitamin $D_3$;
19-nor-24-dihomo-1,25-dihydroxyvitamin $D_3$;
19-nor-24-trihomo-1,25-dihydroxyvitamin $D_3$;
19-nor-26,27-dimethyl-24-homo-1,25-dihydroxyvitamin $D_3$;
19-nor-26,27-dimethyl-24-dihomo-1,25-dihydroxyvitamin $D_3$;
19-nor-26,27-dimethyl-24-trihomo-1,25-dihydroxyvitamin $D_3$;
19-nor-26,27-diethyl-24-homo-1,25-dihydroxyvitamin $D_3$;
19-nor-26,27-diethyl-24-dihomo-1,25-dihydroxyvitamin $D_3$;
19-nor-26,27-diehtyl-24-trihomo-1,25-dihydroxyvitamin $D_3$;
19-nor-26,27-dipropyl-24-homo-1,25-dihydroxyvitamin $D_3$;
19-nor-26,27-dipropyl-24-dihomo-1,25-dihydroxyvitamin $D_3$; and
19-nor-26,27-dipropyl-24-trihomo-1,25-dihydroxyvitamin $D_3$.

For treatment purposes, the novel compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally or transdermally. The compounds are advantageously administered by injection or by intravenous infusion or suitable sterile solutions, or in the form of liquid oral doses or solid doses via the alimentary canal, or in the form of creams, ointments, patches, or similar vehicles suitable for transdermal applications. Doses of from 0.01 μg to 100 μg per day, preferably 0.1 μg to 50 μg per day, of the compounds are appropriate for treatment purposes, such doses being adjusted according to the disease to be treated, its severity and the response of the subject as is well understood in the art. Since the new compounds exhibit specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned cell differentiation treatments, e.g. psoriasis and other malignancies comprise an effective amount of one or more vitamin D compound as defined by the above formula I as the active ingredient, and a suitable carrier. An effective amount of such compounds for use in accordance with this invention is from about 0.01 μg to about 100 μg per gm of composition, and may be administered topically, transdermally, orally or parenterally in dosages of from about 0.1 μg/day to about 100 μg/day.

The compounds may be formulated as creams, lotions, ointments, topical patches, pills, capsules or tablets, or in liquid form as solutions, emulsions, dispersions, or suspensions in pharmaceutically innocuous and acceptable solvents or oils, and such preparations may contain in addition other pharmaceutically innocuous or beneficial components, such as stabilizers, antioxidants, emulsifiers, coloring agents, binders or taste-modifying agents.

The compounds are advantageously administered in amounts sufficient to effect the differentiation of promyelocytes to normal macrophages. Dosages are described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100 μ.

The formulations may conveniently be presented in dosage unit form and may be prepared by any of the methods well known in the art of pharmacy. The term "dosage unit" is meant a unitary, i.e. a single dose which is capable of being administered to a patient as a physically and chemically stable unit dose comprising either the active ingredient as such or a mixture of it with solid or liquid pharmaceutical diluentes or carriers.

In its broadest application, the present invention relates to any analog of vitamin D which have the vitamin D nucleus. By "vitamin D nucleus", it is meant a central part consisting of a substituted chain of five carbon atoms which correspond to positions 8, 14, 13, 17 and 20 of vitamin $D_3$ and at the ends of which are connected at position 20 a structural moiety representing any of the typical side chains known for vitamin D type compounds (such as R as previously defined herein), and at position 8 the 5,7-diene moiety connected to the A-ring of an active 1α-hydroxy vitamin D analog (as illustrated by formula I herein). Thus, various known modifications to the six-membered C-ring and the five-membered D-ring typically present in vitamin $D_3$ such as the lack of one or the other or both, are also embraced by the present invention.

Accordingly, compounds of the following formulae Ia, are along with those of formula I, also encompassed by the present invention:

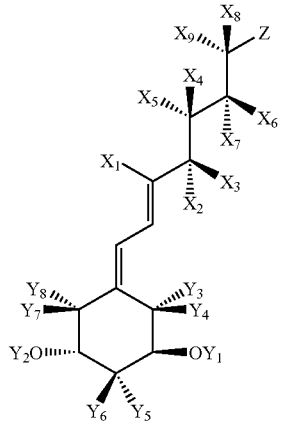

Ia

In the above formula Ia, the definitions of $Y_1$, $Y_2$, $Y_3$, $Y_4$, $Y_5$, $Y_6$, $Y_7$, $Y_8$ and Z are as previously set forth herein. With respect to $X_1$, $X_2$, $X_3$, $X_4$, $X_5$, $X_6$, $X_7$, $X_8$ and $X_9$, these substituents may be the same or different and are selected from hydrogen or lower alkyl, i.e. a $C_{1-5}$ alkyl such as methyl, ethyl or n-propyl. In addition, paired substituents $X_1$ and $X_4$ or $X_5$, $X_2$ or $X_3$ and $X_6$ or $X_7$, $X_4$ or $X_5$ and $X_8$ or $X_9$, when taken together with the three adjacent carbon atoms of the central part of the compound, which correspond to positions 8, 14, 13 or 14, 13, 17 or 13, 17, 20 respectively, can be the same or different and form a saturated or unsaturated, substituted or unsubstituted, carbocyclic 3, 4, 5, 6 or 7 membered ring.

Preferred compounds of the present invention may be represented by one of the following formulae:

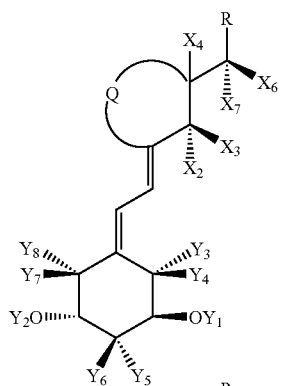

Ib

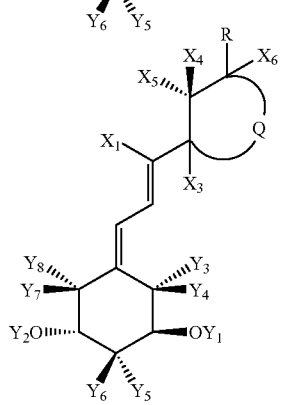

Ic

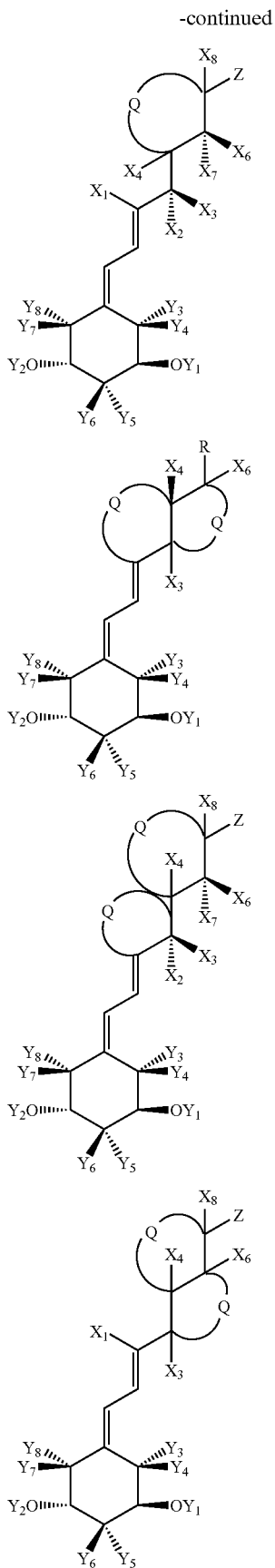

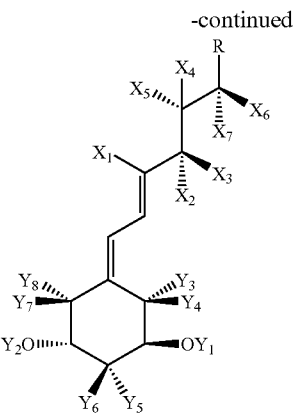

In the above formulae Ib, Ic, Id, Ie, If, Ig and Ih, the definitions of $Y_1$, $Y_2$, $Y_3$, $Y_4$, $Y_5$, $Y_6$, $Y_7$, $Y_8$, R, Z, $X_1$, $X_2$, $X_3$, $X_4$, $X_5$, $X_6$, $X_7$ and $X_8$ are as previously set forth herein. The substituent Q represents a saturated or unsaturated, substituted or unsubstituted, hydrocarbon chain comprised of 0, 1, 2, 3 or 4 carbon atoms, but is preferably the group —$(CH_2)_k$— where k is an integer equal to 2 or 3.

Methods for making compounds of formulae Ia–Ih are known. Specifically, reference is made to International Application Number PCT/EP94/02294 filed 7 Jul. 1994 and published 19 Jan. 1995 under International Publication Number WO95/01960.

We claim:

1. A compound having the formula:

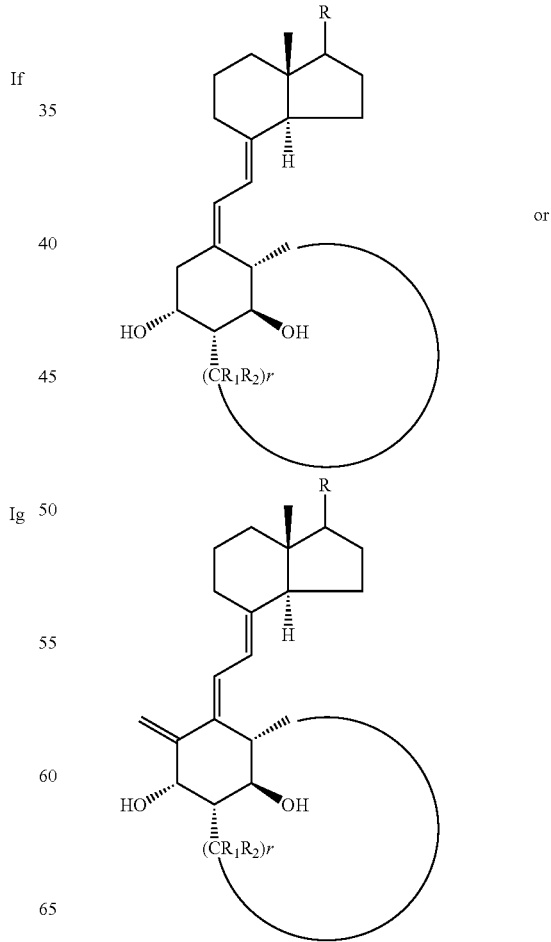

where $R_1$ and $R_2$ are each independently selected from the group consisting of hydrogen, alkyl, hydroxyalkyl, aminoalkyl, halogenalkyl, alkoxyalkyl, aryloxyalkyl, aryl, halogen, hydroxyl, protected hydroxy, alkoxyl, aryloxyl, acyl, an amino group, an amino group substituted with alkyl or aryl substituents and where $R_1$ and $R_2$, taken together, represent an oxo group, or a group —$(CH_2)_m$— where m is an integer having a value of from 2 to 5; and wherein r is an integer having a value of from 1 to 5, an oxygen, sulfur or nitrogen atom may be replaced by an oxygen, sulfur or nitrogen atom; and R is represented by the structure below

where the stereochemical center at carbon 20 may have the R or S configuration, and where Z is selected from Y, —OY, —$CH_2OY$, —C≡CY and —CH═CHY, where the double bond may have the cis or trans geometry, and where Y is selected from hydrogen, methyl, —$COR_{10}$ and a radical of the structure:

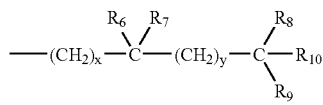

where x and y, independently, represent the integers from 0 to 5, where $R_6$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R_7$, $R_8$, and $R_9$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R_6$ and $R_7$, taken together, represent an oxo group, or an alkylidene group, ═$CR_7R_8$, or the group —$(CH_2)_p$—, where p is an integer from 2 to 5, and where $R_8$ and $R_9$, taken together, represent an oxo group, or the group —$(CH_2)_q$—, where q is an integer from 2 to 5, and where $R_{10}$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —$CH(CH_3)$—, —$(CH_2)_x$—, —$(CR_6R_7)$— or —$(CH_2)_y$— at positions 20, 22, and 23, respectively, may be replaced by an oxygen or sulfur atom.

2. A pharmaceutical composition containing an effective amount of at least one compound as claimed in claim 1 together with a pharmaceutically acceptable excipient.

3. The pharmaceutical composition of claim 2 in dosage unit form.

4. The pharmaceutical composition of claim 3 containing about 0.01 μg to about 100 μg of said at least one compound.

5. The pharmaceutical composition of claim 2 in topical form.

6. The pharmaceutical composition of claim 2 in oral form.

7. A method of treating metabolic bone disease where it is desired to maintain or increase bone mass comprising administering to a patient with said disease an effective amount of a compound as claimed in claim 1.

8. The method of claim 7 where the disease is senile osteoporosis.

9. The method of claim 7 where the disease is postmenopausal osteoporosis.

10. The method of claim 7 where the disease is steroid-induced osteoporosis.

11. The method of claim 7 where the disease is low bone turnover osteoporosis.

12. The method of claim 7 where the disease is osteomalacia.

13. The method of claim 7 where the disease is renal osteodystrophy.

14. The method of claim 7 where the disease is rickets.

15. The method of claim 7 where the disease is vitamin D resistant rickets.

16. The method of claim 7 wherein the compound is administered orally.

17. The method of claim 7 wherein the compound is administered parenterally.

18. The method of claim 7 wherein the compound is administered transdermally.

19. The method of claim 7 wherein the compound is administered in a dosage of from 0.1 μg to 50 μg per day.

* * * * *